United States Patent [19]

Kirsch et al.

[11] Patent Number: 5,132,212
[45] Date of Patent: Jul. 21, 1992

[54] SCL GENE, AND A HEMATOPOIETIC GROWTH AND DIFFERENTIATION FACTOR ENCODED THEREBY

[75] Inventors: Ilan R. Kirsch, Potomac, Md.; C. Glenn Begley, Victoria, Australia

[73] Assignee: The United States of America as represented by the Secretary of the Department of Health and Human Services, Washington, D.C.

[21] Appl. No.: 437,819

[22] Filed: Nov. 17, 1989

[51] Int. Cl.⁵ .................. C12P 21/06; C12N 1/20; C07H 15/12

[52] U.S. Cl. .................. 435/69.4; 435/71.2; 435/252.33; 536/275

[58] Field of Search ............ 435/69.1, 70.1, 172.1, 435/240.1, 240.2; 530/350, 351; 935/1, 9, 18, 23, 34, 38

[56] References Cited

U.S. PATENT DOCUMENTS

| | | | |
|---|---|---|---|
| 4,808,611 | 2/1989 | Cosman | 514/12 |
| 4,810,643 | 7/1989 | Souza | 435/68 |
| 4,879,227 | 11/1989 | Clark | 435/70 |

OTHER PUBLICATIONS

Maniatis, et al 1982 Molecular Cloning A Laboratory Manul C.S.H.L.
Murre et al, Cell, vol. 58, pp. 537-544 (Aug. 11, 1989).
Murre et al, Cell, vol. 56, pp. 777-783 (Mar. 10, 1989).
Begley et al, Proc. Natl. Acad. Sci. U.S.A., vol. 86, pp. 2031-2035 (Mar. 1989).
Mellentin et al, Cell, vol. 58, pp. 77-83 (Jul. 14, 1989).

Primary Examiner—Elizabeth C. Weimar
Assistant Examiner—Deborah Crouch
Attorney, Agent, or Firm—Birch, Stewart, Kolasch & Birch

[57] ABSTRACT

We have identified a new human gene, SCL. We discovered this gene because of its involvement in a chromosomal translocation associated with the occurrence of a stem cell leukemia manifesting myeloid and lymphoid differentiation capabilities. Here we report the sequence of a cDNA for the normal SCL transcript, as well as for an aberrant fusion transcript produced in the leukemic cells. Although different at their 3' untranslated regions, both cDNAs predict a protein with primary amino acid sequence homology to the previously described amphipathic helix-loop-helix DNA binding and dimerization motif of the Lyl-1, myc, MyoD, Ig enhancer binding, daughterless, and achaete-scute families of genes. For these cDNAs, two forms of the SCL protein (greater than 20 and 30 kD) are predicted, both of which retain this putative DNA binding domain. The pattern of expression of SCL mRNA is primarily predominant in early hematopoietic tissues. Taken together, these studies lead to the speculation that SCL plays a role in differentiation and/or commitment events during hematopoiesis.

13 Claims, 14 Drawing Sheets

```
AGTCAGAGTCACTTTCTGTAAATGGTACTTAGGTAGGCGCGTCCGCCTCG
GTTACAGCGGAGCTGCCCGGCGACGGCCGC

ATG GTG CAG CTG AGT CCT CCC GCG CTG GCT GCC CCC GCC
MET Val Gln Leu Ser Pro Pro Ala Leu Ala Ala Pro Ala

GCC CCC GGC CGC GCG CTG CTC TAC AGC CTC AGC CAG CCG
Ala Pro Gly Arg Ala Leu Leu Tyr Ser Leu Ser Gln Pro

CTG GCC TCT CTC GGC AGC GGG TTC TTT GGG GAG CCG GAT
Leu Ala Ser Leu Gly Ser Gly Phe Phe Gly Glu Pro Asp

GCC TTC CCT ATG TTC ACC ACC AAC AAT CGA GTG AAG AGG
Ala Phe Pro MET Phe Thr Thr Asn Asn Arg Val Lys Arg

AGA CCT TCC CCC TAT GAG ATG GAG ATT ACT GAT GGT CCC
Arg Pro Ser Pro Tyr Glu MET Glu Ile Thr Asp Gly Pro

CAC ACC AAA GTT GTG CGG CGT ATC TTC ACC AAC AGC CGG
His Thr Lys Val Val Arg Arg Ile Phe Thr Asn Ser Arg

GAG CGA TGG CGG CAG CAG AAT GTG AAC GGG GCC TTT GCC
Glu Arg Trp Arg Gln Gln Asn Val Asn Gly Ala Phe Ala

GAG CTC CGC AAG CTG ATC CCC ACA CAT CCC CCG GAC AAG
Glu Leu Arg Lys Leu Ile Pro Thr His Pro Pro Asp Lys

AAG CTC AGC AAG AAT GAG ATC CTC CGC CTG GCC ATG AAG
Lys Leu Ser Lys Asn Glu Ile Leu Arg Leu Ala MET Lys

TAT ATC AAC TTC TTG GCC AAG CTG CTC AAT GAC CAG GAG
Tyr Ile Asn Phe Leu Ala Lys Leu Leu Asn Asp Gln Glu

GAG GAG GGC ACC CAG CGG GCC AAG ACT GGC AAG GAC CCT
Glu Glu Gly Thr Gln Arg Ala Lys Thr Gly Lys Asp Pro

GTG GTG GGG GCT GGT GGG GGT GGA GGT GGG GGA GGG GGC
Val Val Gly Ala Gly Gly Gly Gly Gly Gly Gly Gly Gly

GGC GCG CCC CCA GAT GAC CTC CTG CAA GAC GTG CTT TCC
Gly Ala Pro Pro Asp Asp Leu Leu Gln Asp Val Leu Ser

CCC AAC TCC AGC TGC GGC AGC TCC CTG GAT GGG GCA GCC
Pro Asn Ser Ser Cys Gly Ser Ser Leu Asp Gly Ala Ala

AGC CCG GAC AGC TAC ACG GAG GAG CCC GCG CCC AAG CAC
Ser Pro Asp Ser Tyr Thr Glu Glu Pro Ala Pro Lys His

ACG GCC CGC AGC CTC CAT CCT GCC ATG CTG CCT GCC GCC
Thr Ala Arg Ser Leu His Pro Ala MET Leu Pro Ala Ala
```

FIG. 2A

```
GAT GGA GCC GGC CCT CGG TGA
Asp Gly Ala Gly Pro Arg TER

TGGGTCTGGGCCACCAGGATCAGCCAGGA

GGGCGTTCTTAGGCTGCTGGGATGGTGGGCTTCAGGGCAGGTGGGGTGAG

AATTGGGCGGCTCTGAAGCAAGGCGGTGGACTTGAACTTTCCTGGATGTC

TGAACTTTGGGAAGCCTTTACTGACCCTGGGGCTGGCTTTTCTGTTTCCT

GTACCAGTAGGAGATCAGAAAAATGGAGCAAAGTGGTAGGTACTTTTGT

GAAGACGGCACGGTCTTCCCTCTTCCCTCAGTCCCAAATCCTTCCCAAGT

AAGAGGCTGGAGTTGTCACTGCTTTTGGCCTGGAGTTTGGGATCCCTGTC

TTTCCTAAGACCTGGGGTTGTCAGCTCTCATCTGAGGCATCCAGCAGTCT

CTGCCTTGCCTTTAGCCCCTCCCAAGCTGGCTGGGGTGGCCTGTGTGGCC

ACTTCTGTCCATATTTATAGGTACCCAATAGCTGCCCATTTCGTGAGCCC

CATCTTCACCCAGGCCTATGTTGATCCATCCAGCTTGCCAGATGCTGCAG

AGTCACAAGCCTCGAGGTGCCTTCTTCAGGGCCTGGTTGAAGAAGATGAT

CAGTGGACAGTCTGCTCTAGATGAGCTGGGCCGGAGGGTCAGGAAACCCA

GTCGCCCTTACTTCTTGCCCTGGGGATCAAAGTTCTGCTTTCTCCCCAAT

GAGACTTGCCTTCCTAAGCCTGTGGCTGTGGAGACCATGTCTGCAGCCCT

GAGAAAGCCCTGTCGGGCTTTGTGTGAAGGCAGAGAAGGGACAATGATA

GTAGAGTGATATGGAGCAAGAGATATTTGGGCATGTGGGCTTCAACTCC

TCGACATCACTGTTCATGCTGGCGAGTGAATGCCAGTGTGCTGATGGGCG

TACGCTGGTGCTGAGTAGATGCGCAGCCCCATCTGTGCATTCTCCTGGAT

GCTTAGAGGGATTTCTTTGCTGTAAGATGTCTGTTTGCTGATGGTCTGGT

CTATGTTCCGAATTGAGCACAAAACCTGTCCTATGAATGCTTTGCATTTG

GAATTTTGCTTGACTTCAGTTATTGGTGGAATCTTTAGCGCTCAATAGG

ACCAGGATCCAGCCTCACTTCTAGGGTATGGGAAATCCAATCAGAGACCA

GGCCCTGGCTAAGACCCAAACATATGCACATTCACTTAGCAGAACCTTAA

ACACCCCTCAGTTGTGCAGCTTTTGGTCATCAAGGGTGCGTCTGGGAGGT

TGGTTTAATGCAATAGAAGTGCTCCCCTCTGAAAGTTGTACATGAAATTT
```

FIG. 2B

```
TTGTAAATCACATCCTTATCCTTCATCTTTTAAAGAAATAACCACTGCAA

GTCCTTTTGTAAAGTGAAGAATCCTTTTGTAGAATGAACCACTGCCCCTT

CATTGATTTCCTGTGTCAATCCAGATGGTGGGATGTGGTTTTCTTAAGGT

GAGGCCTGTCTGTGACCTGCATCTAAGCCCATGGGACAAATTGCACAGAA

GTCCTGTATGTCTGTCATTGTACCCTTAAGTCACCCTAGCCCTCTCCCTC

TAGGCTCTGCCTTCGAGGTCAGAGGAGAGATAGCCTGTGGCCCTGTCCTG

CCATGCAAGAACTCATCACTGTGGCTGTCTGGAAAGCCCCCCCTTATAGT

TTGGGCTTCAGCCTAGTGGCTTGTCCTCACCATGATGGGGCCCTAATTCA

GCCATGTACAGACAGAGAATATGTCTGCTCCTTTCCCCTTCCTTTTAAGT

AAGGTCCAATTCTCGAGCTTGGGGCAACATTGTTCACCTTTGTAGCACTC

AGGCTCTCCATTCAATTTCAGGCTCCCCAGATCATGTTTTGGTGAAAATT

AGGGTTGGTTCCTTTCCAACGTTTGGAAGATCCTGTGAGGAGCCCCATCT

GTCTAAAGATAGAGTCATTGCTGTAGGATCTAAGGCTGTTTGCTTCACCG

TGGATTCGCTTGAGTTAGGAATGAGAAGTAGCCACAGTATGGATGGGTGG

ATGGGTTTTATGAGATGGATCACATATTTTATTAAGAACTCAAACTTCTG

GCTCCCTCTTCTTTCAGACTTGCCATGTGACTCTGGCTTGGCCTATCTCC

TAGGGCTATGGTGTGGACTGAATGGGATCATGAAAGTAGACAGTTTTGAG

AACGTAAAGAACTTTTTCTTTTCCCTCAATCTCAATCCTGCAGTGGGGTT

TCGCAGCCTGAGTCCACGACCTAGGCAGTAGGCCGGTGTGCCTGACTGCC

CAGCATTTGGGTAATTTAGATTGTAAACCGCTTTGGCCTGAGTTATTGAG

ATTGTCCTCATTTCTCCAGATTATCTATTTGTGTGTGTGTGTGTGTGTGT

GTGAGAGACGGTGTCTTGTTCTGTCACTCAGGCTGGAGTACAGTGGTGCC

ATCATTGCTGTCTGCAGCCTTGAACTCTGGGCTCAAGCAATCCTCTCACC

TCAGCCTCCCGAGTAGGGAGGACCACAGGTGTGAGCCACCACACCTGGCT

AATTTTTACTTTTTTTTTTTTTGGTAGAGATGGAGTCTTGCTATATTGC

CCAGGCTGGTCTTGAAGTCCTGGCTTCAGGCAATTCTCCTGCCTTTGCCT

CCAGAAGCACTGGGATCACAGGTGTCAGCCATTGCACCCAGCCCAGATTG
```

FIG. 2C

```
TCTTAATTTCTATCTTGTTCCAAGGCCAGGGACAGTAATAAGAATGGAAA
AGAGATATGGGAACACTGGCAGACTGTGTAAAATGTAATGCAACTACCCA
AAACAAGCCTGGTAGGAAAGGGCAAGTCTTTAGGTCTTTGTAAGAACTAA
AGAAGATCTGTAATTTTTATTTTCACCCTCTGTACCCCATGACTTTATCC
TTCCTCTCCTTCCTTGTTACCCATGAAAAACTGGCAACATTCCAAGAATA
GCATCTGTACAAAGGGGAAGAACATAAAGGTAAAACAAAACAAAACAAC
ATTTTGAGAACAAAGATGACCATAACCACTGAAGGGAATCACATCTTTTA
AGACAAATTCATATTCTTTTATTTGTTATGGCAGATGACAAGATGGTACA
ACCTTTATTCTTTTCCAAAATAAAACAAAGGGCACAGCATCTGTAGTCAG
CCGACAACTCTTTCGGCCTTTTGGGGGTGGGTCTGGCCGTACTTGTGATT
TCGATGGTACGTGACCCTCTGCTGAAGACTTGCCCCCTGCCCGTGTACAT
AGTGCATTGTTTCTGTGGGCGGGCCCAGCACTTTCCGTCAACGTTGTACT
GTATGTGATGAATTGCGTTGGTCTCTGCATTTTTCTGCAGAAGAGGAGTA
ACCGCTCCAGGTACCTTGACCTTTGTACAGCCCAGAGGCCAACACTGTGG
GTGTGTGACTCTTTAGCAAAAAAAACCCATGTGGTGATGATGTGTCTATA
TATGTGAGGATGTATCGGGAAGATTTCTAAATAAAAGTTTTACAAAGGGA
AAAAAAAAAAAAAAAAAAAAAAAAAAAAAAAAAAAAAAAA
```

FIG. 2D

```
AGG GGC CGG GCC GCC GCC GCT CAG GAC CGG GCC TCA
Arg Gly Arg Ala Ala Ala Ala Gln Asp Arg Ala Ser

AAA TGG CCA CAC GCG TAC CCC CGT AGC GGA AAA ACC
Lys Trp Pro His Ala Tyr Pro Arg Ser Gly Lys Thr

GGG TTC TTT GGG GAG CCG GAT GCC TTC CCT ATG TTC
Gly Phe Phe Gly Glu Pro Asp Ala Phe Pro MET Phe

ACC ACC AAC AAT CGA GTG AAG AGG AGA CCT TCC CCC
Thr Thr Asn Asn Arg Val Lys Arg Arg Pro Ser Pro

TAT GAG ATG GAG ATT ACT GAT GGT CCC CAC ACC AAA
Tyr Glu MET Glu Ile Thr Asp Gly Pro His Thr Lys

GTT GTG CGG CGT ATC TTC ACC AAC AGC CGG GAG CGA
Val Val Arg Arg Ile Phe Thr Asn Ser Arg Glu Arg

TGG CGG CAG CAG AAT GTG AAC GGG GCC TTT GCC GAG
Trp Arg Gln Gln Asn Val Asn Gly Ala Phe Ala Glu

CTC CGC AAG CTG ATC CCC ACA CAT CCC CCG GAC AAG
Leu Arg Lys Leu Ile Pro Thr His Pro Pro Asp Lys

AAG CTC AGC AAG AAT GAG ATC CTC CGC CTG GCC ATG
Lys Leu Ser Lys Asn Glu Ile Leu Arg Leu Ala MET

AAG TAT ATC AAC TTC TTG GCC AAG CTG CTC AAT GAC
Lys Tyr Ile Asn Phe Leu Ala Lys Leu Leu Asn Asp

CAG GAG GAG GAG GGC ACC CAG CGG GCC AAG ACT GGC
Gln Glu Glu Glu Gly Thr Gln Arg Ala Lys Thr Gly

AAG GAC CCT GTG GTG GGG GCT GGT GGG GGT GGA GGT
Lys Asp Pro Val Val Gly Ala Gly Gly Gly Gly Gly

GGG GGA GGG GGC GGC GCG CCC CCA GAT GAC CTC CTG
Gly Gly Gly Gly Gly Ala Pro Pro Asp Asp Leu Leu

CAA GAC GTG CTT TCC CCC AAC TCC AGC TGC GGC AGC
Gln Asp Val Leu Ser Pro Asn Ser Ser Cys Gly Ser

TCC CTG GAT GGG GCA GCC AGC CCG GAC AGC TAC ACG
Ser Leu Asp Gly Ala Ala Ser Pro Asp Ser Tyr Thr

GAG GAG CCC GCG CCC AAG CAC ACG GCC CGC AGC CTC
Glu Glu Pro Ala Pro Lys His Thr Ala Arg Ser Leu

CAT CCT GCC ATG CTG CCT GCC GCC GAT GGA GCC GGC
His Pro Ala MET Leu Pro Ala Ala Asp Gly Ala Gly

CCT CGG TGA
Pro Arg TER
```

FIG. 3A

```
TGGGTCTGGGCCACCAGGATCAGCCAGGA
GGGCGTTCTTAGGCTGCTGGGATGGTGGGCTTCAGGGCAGGTGGGGTGAG
AATTGGGCGGCTCTGAAGCAAGGCGGTGGACTTGAACTTTCCTGGATGTC
TGAACTTTGGGAAGCCTTTACTGACCCTGGGGCTGGCTTTTCTGTTTCCT
GTACCAGTAGGAGATCAGAAAAATGGAGCAAAGTGGTAGGTACTTTTTGT
GAAGACGGCACGGTCTTCCCTCTTCCCTCAGTCCCAAATCCTTCCCAAGT
AAGAGGCTGGAGTTGTCACTGCTTTTGGCCTGGAGTTTGGGATCCCTGTC
TTTCCTAAGACCTGGGGTTGTCAGCTCTCATCTGAGGCATCCAGCAGTCT
CTGCCTTGCCTTTAGCCCCTCCCAAGCTGGCTGGGGTGGCCTGTGTGGCC
ACTTCTGTCCATATTTATAGGTACCCAATAGCTGCCCATTTCGTGAGCCC
CATCTTCACCCAGGCCTATGTTGATCCATCCAGCTTGCCAGATGCTGCAG
AGTCACAAGCCTCGAGGTGCCTTCTTCAGGGCCTGGTTGAAGAAGATGAT
CAGTGGACAGTCTGCTCTAGATGAGCTGGGCCGGAGGGTCAGGAAACCCA
GTCGCCCTTACTTCTTGCCCTGGGGATCAAAGTTCTGCTTTCTCCCCAAT
GAGACTTGCCTTCCTAAGCCTGTGGCTGTGGAGACCATGTCTGCAGCCCT
GAGAAAGCCCTGTCGGGCTTTGTGTGAAGGCAGAGAAAGGGACAATGATA
GTAGAGTGATATGGAGCAAGAGATATTTTGGGCATGTGGGCTTCAACTCC
TCGACATCACTGTTCATGCTGGCGAGTGAATGCCAGTGTGCTGATGGGCG
TACGCTGGTGCTGAGTAGATGCGCAGCCCCATCTGTGCATTCTCCTGGAT
GCTTAGAGGGATTTCTTTGCTGTAAGATGTCTGTTTGCTGATGGTCTGGT
CTATGTTCCGAATTGAGCACAAAACCTGTCCTATGAATGCTTTGCATTTG
GAATTTTTGCTTGACTTCAGTTATTGGTGGAATCTTTAGCGCTCAATAGG
ACCAGGATCCAGCCTCACTTCTAGGGTATGGGAAATCCAATCAGAGACCA
GGCCCTGGCTAAGACCCAAACATATGCACATTCACTTAGCAGAACCTTAA
ACACCCCTCAGTTGTGCAGCTTTTGGTCATCAAGGGTGCGTCTGGGAGGT
TGGTTTAATGCAATAGAAGTGCTCCCCTCTGAAAGTTGTACATGAAATTT
TTGTAAATCACATCCTTATCCTTCATCTTTTAAAGAAATAACCACTGCAA
```

FIG. 3B

GTCCTTTTGTAAAGTGAAGAATCCTTTTGTAGAATGAACCACTGCCCCTT

CATTGATTTCCTGTGTCAATCCAGATGGTGGGATGTGGTTTTCTTAAGGT

GAGGCCTGTCTGTGACCTGCATCTAAGCCCATGGGACAAATTGCACAGAA

GTCCTGTATGTCTGTCATTGTACCCTTAAGTCACCCTAGCCCTCTCCCTC

TAGGCTCTGCCTTCGAGGTCAGAGGAGAGATAGCCTGTGGCCCTGTCCTG

CCATGCAAGAACTCATCACTGTGGCTGTCTGGAAAGCCCCCCCTTATAGT

TTGGGCTTCAGCCTAGTGGCTTGTCCTCACCATGATGGGGCCCTAATTCA

GCCATGTACAGACAGAGAATATGTCTGCTCCTTTCCCCTTCCTTTTAAGT

AAGGTCCAATTCTCGAGCTTGGGGCAACATTGTTCACCTTTGTAGCACTC

AGGCTCTCCATTCAATTTCAGGCTCCCCAGATCATGTTTTGGTGAAAATT

AGGGTTGGTTCCTTTCCAACGTTTGGAAGATCCTGTGAGGAGCCCCATCT

GTCTAAAGATAGAGTCATTGCTGTAGGATCTAAGGCTGTTTGCTTCACCG

TGGATTCGCTTGAGTTAGGAATGAGAAGTAGCCACAGTATGGATGGGTGG

ATGGGTTTTATGAGATGGATCACATATTTTATTAAGAACTCAAACTTCTG

GCTCCCTCTTCTTTCAGACTTGCCATGTGACTCTGGCTTGGCCTATCTCC

TAGGGCTATGGTGTGGACTGAATGGGATCATGAAAGTAGACAGTTTTGAG

AACGTAAAGAACTTTTTCTTTTCCCTCAATCTCAATCCTGCAGTGGGGTT

TCGCAGCCTGAGTCCACGACCTAGGCAGTAGGCCGGTGTGCCTGACTGCC

CAGCATTTGGGTAATTTAGATTGTAAACCGCTTTGGCCTGAGTTATTGAG

ATTGTCCTCATTTCTCCAGATTATCTATTTGTGTGTGTGTGTGTGTGTGT

GTGAGAGACGGTGTCTTGTTCTGTCACTCAGGCTGGAGTACAGTGGTGCC

ATCATTGCTGTCTGCAGCCTTGAACTCTGGGCTCAAGCAATCCTCTCACC

TCAGCCTCCCGAGTAGGGAGGACCACAGGTGTGAGCCACCACACCTGGCT

AATTTTACTTTTTTTTTTTTGGTAGAGATGGAGTCTTGCTATATTGC

CCAGGCTGGTCTTGAAGTCCTGGCTTCAGGCAATTCTCCTGCCTTTGCCT

CCAGAAGCACTGGGATCACAGGTGTCAGCCATTGCACCCAGCCCAGATTG

TCTTAATTTCTATCTTGTTCCAAGGCCAGGGACAGTAATAAGAATGGAAA

FIG. 3C

```
AGAGATATGGGAACACTGGCAGACTGTGTAAAATGTAATGCAACTACCCA
AAACAAGCCTGGTAGGAAAGGGCAAGTCTTTAGGTCTTTGTAAGAACTAA
AGAAGATCTGTAATTTTTATTTTCACCCTCTGTACCCCATGACCTTATCC
TTCCTCTCCTTCCTTGTTACCCATGAAAAACTGGCAACATTCCAAGAATA
GCATCTGTACAAAGGGGAAAGAACATAAAGGTAAAACAAAACAAAACAAC
ATTTTGAGAACAAAGATGACCATAACCACTGAAGGGAATCACATCTTTTA
AGACAAATTCATATTCTTTTATTTGTTATGGCAGATGACAAGATGGTACA
ACCTTTATTCTTTTCCAAAATAAAACAAAGGGCACAGCATCTGTAGTCAG
CCGACAACTCTTTCGGCCTTTTGGGGGTGGGTCTGGCCGTACTTGTGATT
TCGATGGTACGTGACCCTCTGCTGAAGACTTGCCCCCTGCCCGTGTACAT
AGTGCATTGTTTCTGTGGGCGGGCCCAGCACTTTCCGTCAACGTTGTACT
GTATGTGATGAATTGCGTTGGTCTCTGCATTTTCTGCAGAAGAGGAGTA
ACCGCTCCAGGTACCTTGACCTTTGTACAGCCCAGAGGCCAACACTGTGG
GTGTGTGACTCTTTAGCAAAAAAAACCCATGTGGTGATGATGTGTCTATA
TATGTGAGGATGTATCGGGAAGATTTCTAAATAAAAGTTTTACAAAGGGA
AAAAAAAAAAAAAAAAAAAAAAAAAAAAAAAAAAAAAAAA
```

FIG. 3D

| | | HYDROPHILIC DOMAIN | AMPHIPATHIC HELIX I | | AMPHIPATHIC HELIX II |
|---|---|---|---|---|---|

SCL: VRRIFTNSRERWRQQNVNGAFAELRKLIPTHP----------PDKKLSKNEILRLAMKYINFLAKLLN

CONSENSUS:
```
           R   N  ER  R   Ψ   F   L   Ψ                    KΨ  IL  AΨ  YΨ  L
                          L                                    T           V  V
```

| | Hydrophilic / Helix I | Helix II |
|---|---|---|
| Lyl-1  | ARRVFTNSRERWRQQNVNGAFAEIRKLLPTHP---------- | PDRKLSKNEVIRLAMKYIGFIVRLLR |
| c-myc  | VKRRTHNVLERQRRNELKRSFFALRDQIP------ELEN---- | NEKAPKVVILKKATAYILSVQAEEQ |
| L-myc  | TKRKNHNFLERKRRNDLRSRFLALRDQVP------TLAS---- | CSKAPKVVILSKALEYLQALVGAEK |
| N-myc  | ERRRNHNILERQRRNDLRSSFLTLRDHVP------ELVK---- | NEKAAKVVILKKATEYVHSLQAEEH |
| MyoD   | DRRKAATMRERRRLSKVNEAFETLKRCTSSNP----------- | NQRLPKVEIIRNAIRYIEGLQALLR |
| E12    | ERRVANNARERLRVRDINEAFKELGRMCQLHLNSEKP------ | --QTKLLILHQAVSVILNLEQQVR |
| twist  | NQRVMANVREROTQSLNDAFKSLQQIIP------TL------- | --QTKLKIATRYIDFLCRMLS |
| da     | ERRQANNARERLRIRDINEALKELGRMCMTHLKSDKP------ | --QTKLGILNMAVEVIMTLEQQVR |
| AS-C T5| VIRR--NARERNRVKQVNNGFSQLRQHIPAAVIADLSNGRRGIGPGANKKLSKVSI | LKMAVEYIRRLQKVLH |
| AS-C T4| VQRR--NARERNRVKQVNNSFARLRQHIPQSIITDLTKG--G-GRGPHKKISKVDTL | RIAVEYIRSLQDLVD |

FIG. 5

```
... ... ACC ACC AAC AAT CGA GTG AAG AGG AGA CCT TCC CCC TAT GAG ATG GAG ATT ACT GAT GGT CCC CAC ACC
... ... Thr Thr Asn Asn Arg Val Lys Arg Arg Pro Ser Pro Tyr Glu Met Glu Ile Thr Asp Gly Pro His Thr
... ... Thr Thr Asn Asn Arg Val Lys Arg Arg Pro Ser Pro Tyr Glu Met Glu Ile Thr Asp Gly Pro His Thr

AAA GTT GTG CGG ATC TTC ACC TTC ATC CGT GTG AAC AGC CGA GAG CGA TGG CGG CAG AAT GTG AAC GGG GCC TTT GCC GAG
Lys Val Val Arg Ile Phe Thr Phe Ile Arg Val Asn Ser Arg Glu Arg Trp Arg Gln Asn Val Asn Gly Ala Phe Ala Glu
Lys Val Val Arg Ile Phe Thr Phe Ile Arg Val Asn Ser Arg Glu Arg Trp Arg Gln Asn Val Asn Gly Ala Phe Ala Glu

CTC CGC AAG CTG ATC CCC ACA CAT CCC ACC CAT CCC CCG GAC AAG AAG CTC AGC AAG AAT GAG ATC CTC GCC ATG AAG
Leu Arg Lys Leu Ile Pro Thr His Pro Thr His Pro Pro Asp Lys Lys Leu Ser Lys Asn Glu Ile Leu Arg Leu Ala Met Lys
Leu Arg Lys Leu Ile Pro Thr His Pro Thr His Pro Pro Asp Lys Lys Leu Ser Lys Asn Glu Ile Leu Arg Leu Ala Met Lys

TAT ATC AAC TTC TTG GCC AAG CTC AAT GAC CTC CTC AAT GAC CAG GAG GAG CAG ACC CGG AAG GCC ACT GGC AAG GAC
Tyr Ile Asn Phe Leu Ala Lys Leu Asn Asp Leu Leu Asn Asp Gln Glu Glu Gln Thr Arg Lys Ala Thr Gly Lys Asp
Tyr Ile Asn Phe Leu Ala Lys Leu Asn Asp Leu Leu Asn Asp Gln Glu Glu Gln Thr Arg Lys Ala Thr Gly Lys Asp [

CCT GTG GGT GCT GGT GGG GGT GGA GGG GGG GCG CCA GAT GAC CTC CTG CAA GAC GTG
Pro Val Gly Ala Gly Gly Gly Gly Gly Gly Gly Ala Pro Asp Asp Leu Leu Gln Asp Val

CTT TCC CCC AAC TCC AGC TGC GGC AGC TCC CTG GAT GGG GCA GCC CCG GAC AGC TAC ACG GAG GAG CCC GCG
Leu Ser Pro Asn Ser Ser Cys Gly Ser Ser Leu Asp Gly Ala Ala Ser Pro Asp Ser Tyr Thr Glu Glu Pro Ala
] Ala Ala Ala Ala Pro Trp Met Gly Gln Pro Ala Arg Thr Ala Thr Arg Arg Ser Pro Arg

CCC AAG CAC ACG GCC GCC AGC GCC CTC CAT CCT GCC ATG CTG CCT GCC GCC GAT GGA GCC GCC GAT GGA GCC GCT CGG TGAT GGG TCT
Pro Lys His Thr Ala Arg Ser Leu His Pro Ala Met Leu Pro Ala Ala Asp Gly Ala Gly Pro Arg TER
Pro Ser Thr Arg Pro Ala Ala Ser Ile Leu Pro Cys Cys Leu Pro Pro Met Glu Pro Ala Leu Gly Asp Gly Ser
```

FIG. 6A

```
GGG CCA CCA GGA TCA GCC AGG AGG GCG TTC TTA GGC TGC TGG GAT GGT GGG CTT CAG GGC AGG TGG GGT GAG AAT
Gly Pro Pro Gly Ser Ala Arg Arg Ala Phe Leu Gly Cys Trp Asp Gly Gly Leu Gln Gly Arg Trp Gly Glu Asn

TGG GCG GCT CTG AAG CAA GGC GGT GGA CTT GAA CTT TCC ATG TCT GAA CTT TGG GAA GCC TTT ACT GAC CCT
Trp Ala Ala Leu Lys Gln Gly Gly Gly Leu Glu Leu Ser Met Ser Glu Leu Trp Glu Ala Phe Thr Asp Pro

GGG GCT GGC TTT TCT GTT TCC TGT ACC AGT AGG AGA TCA GAA AAA TGG AGC AAA GTG GTA GGT ACT TTT TGT GAA
Gly Ala Gly Phe Ser Val Ser Cys Thr Ser Arg Arg Ser Glu Lys Trp Ser Lys Val Val Gly Thr Phe Cys Glu

GAC GGC ACG GTC TTC CCT CTT CCC TCA GTC CCA AAT CCT TCC CAA GTA AGA GGC TGG AGT TGT CAC TGC TTT TGG
Asp Gly Thr Val Phe Pro Leu Pro Ser Val Pro Asn Pro Ser Gln Val Arg Gly Trp Ser Cys His Cys Phe Trp

CCT GGA GTT TGG GAT CCC TGT CTT TCC TAA
Pro Gly Val Trp Asp Pro Cys Leu Ser TER
```

FIG. 6B

```
GACTTGGGGTTGTCAGCTCTCATCTGAGGCATCCAGCAGTCTCTGCCTTAGCCCTGCCTTGGCGGTGGCCTGTGTGGCCACTTCTG
TCCATATTTATAGTACCCAATAGCTGCCATTTGGTGAGCCCATCTTCACCAGGCCTATGTGATCCATCAGCTTGCCAGATGCTGCAGAGTCAC
AAGCCTCGAGGTGCCTTCTTCAGGCCTGGTTGAAGAGATGATCAGTGGACAGTCTGCTCTAGATGAGCTGGCCGGAGGTCAGGAAACCAGTGC
CCTTACTTCTGCCCTGGGATCAAAGTTCTGCTTTCTCCCAATGAGACTTGCCTTCCTAAGCCTCGTGCCTTGTGGAGACCATCTCTGCAGCCCTGAGT
CTTGctggggataCGCaCagtGTCTacaaaacCTAcagaGACCTGtacaaaaactGcagggGCaaaGTGCCatTtcCCtggatATccTCacCCTggg
tccCatgcCtcaggagacaaacacagcaaGCagCagCttCCCtgCCCtgcttTgggCCTgaagGgatagcAggaagtTgaCTgaCCaggagaTgaCCaC
agctgctgaCCtctcaCTCAgctGTgttcTTccttggTGaaCTgCaTTtCTtaCaGaCaCattTGggaATaCaaaAGgcctTtcTt
aaaaaaaaaaa
```

FIG. 6C

SCL GENE, AND A HEMATOPOIETIC GROWTH AND DIFFERENTIATION FACTOR ENCODED THEREBY

BACKGROUND OF THE INVENTION

The study of hematopoiesis is a prototype for the study of cell differentiation in general. A population of stem cells, maintained throughout life, remains capable of self-renewal, as well as commitment to the lymphoid, myeloid, monocytoid, erythroid, or megakaryocytoid lineages. Numerous investigations are now focussed on identifying the critical genes involved in the decisions governing the differentiation of blood-forming cells. Among the expected features of such genes might be their expression at a pivotal time in hematopoietic development. More intensive attention to such a candidate gene might be merited if it appeared to encode a protein whose features were similar to proteins already implicated as playing roles in other eukaryotic developmental systems.

SUMMARY OF THE INVENTION

We have identified a new human gene, SCL. We discovered this gene because of its involvement in a chromosomal translocation associated with the occurrence of a stem cell leukemia manifesting myeloid and lymphoid differentiation capabilities. Here we report the sequence of a cDNA for the normal SCL transcript, as well as for an aberrant fusion transcript produced in the leukemic cells. Although different at their 3' untranslated regions, both cDNAs predict a protein within which is contained a region of primary amino acid sequence homology to the previously described amphipathic helix-loop-helix DNA binding and dimerization motif also contained within a variety of proteins whose role in development, differentiation, and proliferation has already been established. Among these proteins are the Lyl-1, myc, MyoD, Ig enhancer binding, daughterless, and achaete-scute families of genes. The sequence of SCL within this motif is similar but not identical to any of the above mentioned proteins. The pattern of expression of SCL mRNA is primarily predominant in early hematopoietic tissues. Taken together, these studies strongly suggest that SCL plays a role in proliferation, differentiation and/or commitment events during hematopoiesis.

Our approach to the question of cell-type specific gene function is via the cloning and characterization of cell-type specific chromosomal translocations. The rationale behind these efforts is our belief that such translocations often highlight chromosomal regions of differentiated activity in the cells in which they occur (1). This premise has so far seemed particularly obvious in the translocations associated with hematopoietic malignancies (2). It was with this in mind that we undertook the cloning and characterization of a reciprocal translocation, t(1;14) (P33;q11.2), associated with the development of a stem cell leukemia in a 16 year old male. This patient's leukemic cells and the cell line, DU.528, subsequently derived from them, were capable of responding to a variety of inducing agents by changing their phenotypic pattern from that of an early lymphoid cell to that of a cell of myeloid or monocytoid lineage (3). Our study identified a transcript unit on chromosome 1 abutting the translocation breakpoint (4). We called this transcript "SCL" for stem cell leukemia, the tissue in which it was first appreciated. The same probe that identified the transcript also identifies a single copy gene in other mammalian species by Southern blot analysis.

The SCL gene preferably comprises the sequence

```
CGG CGT ATC TTC ACC AAC AGC CGG GAG CGA TGG CGG CAG CAG AAT GTG
AAC GGG GCC TTT GCC GAG CTC CGC AAG CTG ATC CCC ACA CAT CCC CCG
GAC AAG AAG CTC AGC AAG AAT GAG ATC CTC CGC CTG GCC ATG AAG TAT
ATC AAC TTC TTG.
or
ATG GCC CCC CCG CAC CTG GTC CTG CTG AAC GCG TCG CCA AGG AGA CGA
GCC GCC CGG CCG CAG CGG AGC CCC CAG TCA TCG AAC TGG GCG CGC GCG
GAG CCC GGG GGG CGG CCT GCC GGT GGG GGC GGC GCC GCG AGA GAC TTA
AAG GCG GCG ACG CGG CGA CGG CCA AGC GCG CCA TCG GGT GCC CAC CAC
CGA GCT GTG CAG ACC TCC CGG CCC GCC CCG GCC CCC GCG CCC GCC TCG
GTT ACA GCG GAG CTG CCC GGC GAC GGC CGC ATG GTG CAG CTG AGT CCT
CCC GCG CTG GCT GCC CCC GCC GCC CCC GGC CGC GCG CTG CTC TAC AGC
CTC AGC CAG CCG CTG GCC TCT CTC GGC AGC GGG TTC TTT GGG GAG CCG
GAT GCC TTC CCT ATG TTC ACC ACC AAC AAT CGA GTG AAG AGG AGA CCT
TCC CCC TAT GAG ATG GAG ATT ACT GAT GGT CCC CAC ACC AAA GTT GTG
CGG CGT ATC TTC ACC AAC AGC CGG GAG CGA TGG CGG CAG CAG AAT GTG
AAC GGG GCC TTT GCC GAG CTC CGC AAG CTG ATC CCC ACA CAT CCC CCG
GAC AAG AAG CTC AGC AAG AAT GAG ATC CTC CGC CTG GCC ATG AAG TAT
ATC AAC TTC TTG GCC AAG CTG CTC AAT GAC CAG GAG GAG GAG GGC ACC
CAG CGG GCC AAG ACT GGC AAG GAC CCT GTG GTG GGG GCT GGT GGG GGT
GGA GGT GGG GGA GGG GGC GGC GCG CCC CCA GAT GAC CTC CTG CAA GAC
GTG CTT TCC CCC AAC TCC AGC TGC GGC AGC TCC CTG GAT GGG GCA GCC
AGC CCG GAC AGC TAC ACG GAG GAG CCC GCG CCC AAG CAC ACG GCC CGC
AGC CTC CAT CCT GCC ATG CTG CCT GCC GCC GAT GGA GCC GGC CCT CGG
TGA,
or
AGG GGC CGG GCC GCC GCC GCT CAG GAC CGG GCC TCA AAA TGG CCA CAC
GCG TAC CCC CGT AGC GGA AAA ACC GGG TTC TTT GGG GAG CCG GAT GCC
TTC CCT ATG TTC ACC ACC AAC AAT CGA GTG AAG AGG AGA CCT TCC CCC
TAT GAG ATG GAG ATT ACT GAT GGT CCC CAC ACC AAA GTT GTG CGG CGT
ATC TTC ACC AAC AGC CGG GAG CGA TGG CGG CAG CAG AAT GTG AAC GGG
GCC TTT GCC GAG CTC CGC AAG CTG ATC CCC ACA CAT CCC CCG GAC AAG
AAG CTC AGC AAG AAT GAG ATC CTC CGC CTG GCC ATG AAG TAT ATC AAC
TTC TTG GCC AAG CTG CTC AAT GAC CAG GAG GAG GAG GGC ACC CAG CGG
GCC AAG ACT GGC AAG GAC CCT GTG GTG GGG GCT GGT GGG GGT
GGG GGA GGG GGC GGC GCG CCC CCA GAT GAC CTC CTG CAA GAC GTG CTT
TCC CCC AAC TCC AGC TGC GGC AGC TCC CTG GAT GGG GCA GCC AGC CCG
GAC AGC TAC ACG GAG GAG CCC GCG CCC AAG CAC ACG GCC CGC AGC CTC
```

-continued

| | | | | | | | | | | | | | | |
|---|---|---|---|---|---|---|---|---|---|---|---|---|---|---|
| CAT | CCT | GCC | ATG | CTG | CCT | GCC | GCC | GAT | GGA | GCC | GGC | CCT | CGG | TGA |
| or | | | | | | | | | | | | | | |
| ACC | ACC | AAC | AAT | CGA | GTG | AAG | AGG | AGA | CCT | TCC | CCC | TAT | GAG | ATG | GAG |
| ATT | ACT | GAT | GGT | CCC | CAC | ACC | AAA | GTT | GTG | CGG | CGT | ATC | TTC | ACC | AAC |
| AGC | CGG | GAG | CGA | TGG | CGG | CAG | CAG | AAT | GTG | AAC | GGG | GCC | TTT | GCC | GAG |
| CTC | CGC | AAG | CTG | ATC | CCC | ACA | CAT | CCC | CCG | GAC | AAG | AAG | CTC | AGC | AAG |
| AAT | GAG | ATC | CTC | CGC | CTG | GCC | ATG | AAG | TAT | ATC | AAC | TTC | TTG | GCC | AAG |
| CTG | CTC | AAT | GAC | CAG | GAG | GAG | GAG | GGC | ACC | CAG | CGG | GCC | AAG | ACT | GCT |
| GCG | GCA | GCT | CCC | TGG | ATG | GGG | CAG | CCA | GCC | CGG | ACA | GCT | ACA | CGG | AGG |
| AGC | CCG | CGC | CCA | AGC | ACA | CGG | CCC | GCA | GCC | TCC | ATC | CTG | CCA | TGC | TGC |
| CTG | CCA | CCG | ATG | GAG | CCG | GCC | CTC | GGT | GAT | GGG | TCT | GGG | CAA | CAA | GGA |
| TCA | GCC | AGG | AGG | GCG | TCC | TTA | GGC | TGC | TGG | GAT | GGT | GGG | CTT | CAG | GGC |
| AGG | TGG | GGT | GAG | AAT | TGG | GCG | GCT | CTG | AAG | CAA | GGC | GGT | GGA | CTT | GAA |
| CTT | TCC | TGG | ATG | TCT | GAA | CTT | TGG | GAA | GCC | TTT | ACT | GAC | CCT | GGG | GCT |
| GGC | TTT | TCT | GTT | TCC | TGT | ACC | AGT | AGG | AGA | TCA | GAA | AAA | TGG | AGC | AAA |
| GTG | GTA | GGT | ACT | TTT | TGT | GAA | GAC | GGC | ACG | GTC | TTC | CCT | CTT | CCC | TCA |
| GTC | CCA | AAT | CCT | TCC | CAA | GTA | AGA | GGC | TGG | AGT | TGT | CAC | TGC | TTT | TGG |
| CCT | GGA | GTT | TGG | GAT | CCC | TGT | CTT | TCC | TAA. | | | | | | |

The SCL hematopoietic growth and differentiation affector may be purified or isolated. The affector preferably comprises the amino acid sequence A second form of the protein, which includes a different amino terminus comprises the amino acid sequence

| | | | | | | | | | | | | | | |
|---|---|---|---|---|---|---|---|---|---|---|---|---|---|---|
| Arg | Arg | Ile | Phe | Thr | Asn | Ser | Arg | Glu | Arg | Trp | Arg | Gln | Gln | Asn | Val |
| Asn | Gly | Ala | Phe | Ala | Glu | Leu | Arg | Lys | Leu | Ile | Pro | Thr | His | Pro | Pro |
| Asp | Lys | Lys | Leu | Ser | Lys | Asn | Glu | Ile | Leu | Arg | Leu | Ala | Met | Lys | Tyr |
| Ile | Asn | Phe | Leu, | | | | | | | | | | | | |
| | | | or | | | | | | | | | | | | |
| MET | Ala | Pro | Pro | His | Leu | Val | Leu | Leu | Asn | Ala | Ser | Pro | Arg | Arg | Arg |
| Ala | Ala | Arg | Pro | Gln | Arg | Ser | Pro | Gln | Ser | Ser | Asn | Trp | Ala | Arg | Ala |
| Glu | Pro | Gly | Gly | Arg | Pro | Ala | Gly | Gly | Gly | Gly | Ala | Ala | Arg | Asp | Leu |
| Lys | Ala | Ala | Thr | Arg | Arg | Arg | Pro | Ser | Ala | Pro | Ser | Gly | Ala | His | His |
| Arg | Ala | Val | Gln | Thr | Ser | Arg | Pro | Ala | Pro | Ala | Pro | Ala | Pro | Ala | Ser |
| Val | Thr | Ala | Glu | Leu | Pro | Gly | Asp | Gly | Arg | Met | Val | Gln | Leu | Ser | Pro |
| Pro | Ala | Leu | Ala | Ala | Pro | Ala | Ala | Pro | Gly | Arg | Ala | Leu | Leu | Tyr | Ser |
| Leu | Ser | Gln | Pro | Leu | Ala | Ser | Leu | Gly | Ser | Gly | Phe | Phe | Gly | Glu | Pro |
| Asp | Ala | Phe | Pro | Met | Phe | Thr | Thr | Asn | Asn | Arg | Val | Lys | Arg | Arg | Pro |
| Ser | Pro | Tyr | Glu | Met | Glu | Ile | Thr | Asp | Gly | Pro | His | Thr | Lys | Val | Val |
| Arg | Arg | Ile | Phe | Thr | Asn | Ser | Arg | Glu | Arg | Trp | Arg | Gln | Gln | Asn | Val |
| Asn | Gly | Ala | Phe | Ala | Glu | Leu | Arg | Lys | Leu | Ile | Pro | Thr | His | Pro | Pro |
| Asp | Lys | Lys | Leu | Ser | Lys | Asn | Glu | Ile | Leu | Arg | Leu | Ala | Met | Lys | Tyr |
| Ile | Asn | Phe | Leu | Ala | Lys | Leu | Leu | Asn | Asp | Gln | Glu | Glu | Glu | Gly | Thr |
| Gln | Arg | Ala | Lys | Thr | Gly | Lys | Asp | Pro | Val | Val | Gly | Ala | Gly | Gly | Gly |
| Gly | Gly | Gly | Gly | Gly | Gly | Ala | Pro | Pro | Asp | Asp | Leu | Leu | Gln | Asp | |
| Val | Leu | Ser | Pro | Asn | Ser | Ser | Cys | Gly | Ser | Ser | Leu | Asp | Gly | Ala | Ala |
| Ser | Pro | Asp | Ser | Tyr | Thr | Glu | Glu | Pro | Ala | Pro | Lys | His | Thr | Ala | Arg |
| Ser | Leu | His | Pro | Ala | Met | Leu | Pro | Ala | Ala | Asp | Gly | Ala | Gly | Pro | Arg. |

| | | | | | | | | | | | | | | |
|---|---|---|---|---|---|---|---|---|---|---|---|---|---|---|
| Arg | Gly | Arg | Ala | Ala | Ala | Ala | Gln | Asp | Arg | Ala | Ser | Lys | Trp | Pro | His |
| Ala | Tyr | Pro | Arg | Ser | Gly | Lys | Thr | Gly | Phe | Phe | Gly | Glu | Pro | Asp | Ala |
| Phe | Pro | Met | Phe | Thr | Thr | Asn | Asn | Arg | Val | Lys | Arg | Arg | Pro | Ser | Pro |
| Tyr | Glu | Met | Glu | Ile | Thr | Asp | Gly | Pro | His | Thr | Lys | Val | Val | Arg | Arg |
| Ile | Phe | Thr | Asn | Ser | Arg | Glu | Arg | Trp | Arg | Gln | Gln | Asn | Val | Asn | Gly |
| Ala | Phe | Ala | Glu | Leu | Arg | Lys | Leu | Ile | Pro | Thr | His | Pro | Pro | Asp | Lys |
| Lys | Leu | Ser | Lys | Asn | Glu | Ile | Leu | Arg | Leu | Ala | Met | Lys | Tyr | Ile | Asn |
| Phe | Leu | Ala | Lys | Leu | Leu | Asn | Asp | Gln | Glu | Glu | Glu | Gly | Thr | Gln | Arg |
| Ala | Lys | Thr | Gly | Lys | Asp | Pro | Val | Val | Gly | Ala | Gly | Gly | Gly | Gly | Gly |
| Gly | Gly | Gly | Gly | Gly | Ala | Pro | Pro | Asp | Asp | Leu | Leu | Gln | Asp | Val | Leu |
| Ser | Pro | Asn | Ser | Ser | Cys | Gly | Ser | Ser | Leu | Asp | Gly | Ala | Ala | Ser | Pro |
| Asp | Ser | Tyr | Thr | Glu | Glu | Pro | Ala | Pro | Lys | His | Thr | Ala | Arg | Ser | Leu |
| His | Pro | Ala | Met | Leu | Pro | Ala | Ala | Asp | Gly | Ala | Gly | Pro | Arg. | | |

Another form of the protein comprises the amino acid sequence

| | | | | | | | | | | | | | | |
|---|---|---|---|---|---|---|---|---|---|---|---|---|---|---|
| Thr | Thr | Asn | Asn | Arg | Val | Lys | Arg | Arg | Pro | Ser | Pro | Tyr | Glu | Met | Glu |
| Ile | Thr | Asp | Gly | Pro | His | Thr | Lys | Val | Val | Arg | Arg | Ile | Phe | Thr | Asn |
| Ser | Arg | Glu | Arg | Trp | Arg | Gln | Gln | Asn | Val | Asn | Gly | Ala | Phe | Ala | Glu |
| Leu | Arg | Lys | Leu | Ile | Pro | Thr | His | Pro | Pro | Asp | Lys | Lys | Leu | Ser | Lys |
| Asn | Glu | Ile | Leu | Arg | Leu | Ala | Met | Lys | Tyr | Ile | Asn | Phe | Leu | Ala | Lys |
| Leu | Leu | Asn | Asp | Gln | Glu | Glu | Glu | Gly | Thr | Gln | Arg | Ala | Lys | Thr | Ala |
| Ala | Ala | Ala | Pro | Trp | Met | Gly | Gln | Pro | Ala | Arg | Thr | Ala | Thr | Arg | Arg |
| Ser | Pro | Arg | Pro | Ser | Thr | Arg | Pro | Ala | Ala | Ser | Ile | Leu | Pro | Cys | Cys |
| Leu | Pro | Pro | Met | Glu | Pro | Ala | Leu | Gly | Asp | Gly | Ser | Gly | Pro | Pro | Gly |
| Ser | Ala | Arg | Arg | Ala | Phe | Leu | Gly | Cys | Trp | Asp | Gly | Gly | Leu | Gln | Gly |
| Arg | Trp | Gly | Glu | Asn | Trp | Ala | Ala | Leu | Lys | Gln | Gly | Gly | Gly | Leu | Glu |
| Leu | Ser | Trp | Met | Ser | Glu | Leu | Trp | Glu | Ala | Phe | Thr | Asp | Pro | Gly | Ala |
| Gly | Phe | Ser | Val | Ser | Cys | Thr | Ser | Arg | Arg | Ser | Glu | Lys | Trp | Ser | Lys |

| Val | Val | Gly | Thr | Phe | Cys | Glu | Asp | Gly | Thr | Val | Phe | Pro | Leu | Pro | Ser |
| Val | Pro | Asn | Pro | Ser | Gln | Val | Arg | Gly | Trp | Ser | Cys | His | Cys | Phe | Trp |
| Pro | Gly | Val | Trp | Asp | Pro | Cys | Leu | Ser | | | | | | | |

The present invention is also directed to a vector comprising a replicable vector and a DNA sequence corresponding to the above described SCL gene inserted into said vector. The vector may be an expression vector and is conveniently a plasmid.

As mentioned above, the SCL hematopoietic growth and differentiation affector preferably comprises one of the sequences described above or a homologous variant of said affector having less than 8 conservative amino acid changes, preferably less than 5 conservative amino acid changes. In this context, "conservative amino acid changes" are substitutions of one amino acid by another amino acid wherein the charge and polarity of the two amino acids are not fundamentally different. Amino acids can be divided into the following four groups: (1) acidic amino acids, (2) neutral polar amino acids, (3) neutral non-polar amino acids and (4) basic amino acids. Conservative amino acid changes can be made by substituting one amino acid within a group by another amino acid within the same group. Representative amino acids within these groups include, but are not limited to, (1) acidic amino acids such as aspartic acid and glutamic acid, (2) neutral polar amino acids such as valine, isoleucine and leucine, (3) neutral nonpolar amino acids such as asparganine and glutamine and (4) basic amino acids such as lysine, arginine and histidine.

In addition to the above mentioned substitutions, the affector of the present invention may comprise the above mentioned specific amino acid sequences and additional sequences at the N-terminal end, C-terminal end or in the middle thereof. The "gene" or nucleotide sequence may have similar substitutions which allow it to code for the corresponding affector.

In processes for the synthesis of the SCL hematopoietic growth and differentiation affector, DNA which encodes the affector is ligated into a replicable (reproducible) vector, the vector is used to transform host cells, and the affector is recovered from the culture. The host cells for the above-described vectors include gram-negative bacteria such as E. coli, gram-positive bacteria, yeast and mammalian cells. Suitable replicable vectors will be selected depending upon the particular host cell chosen.

For pharmaceutical uses, the SCL hematopoietic growth and differentiation affector is purified, preferably to homogeneity, and then mixed with a compatible pharmaceutically acceptable carrier or diluent. The pharmaceutically acceptable carrier can be a solid or liquid carrier depending upon the desired mode of administration to a patient.

Transgenic non-human mammals such as mice may be constructed by incorporating the SCL gene of the present invention into fertilized mammalian eggs at a very early stage of development whereby the gene is incorporated into the chromosomes of the developing cells. In this way, all or substantially all of the cells of the transgenic mammal will contain the SCL gene.

Figures 1A, 1B:
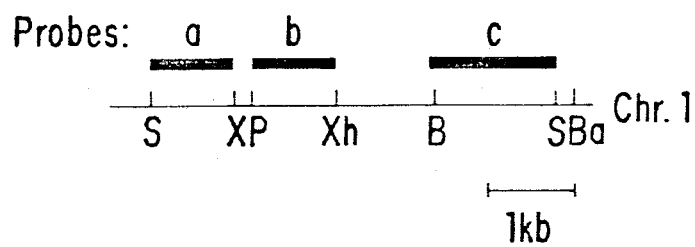
FIGS. 1A-B.

A. Map of germline chromosome 1 showing probes used for Northern blot analysis and for screening the cDNA libraries. B=Bgl II, Ba=Bam HI, P=Pst I, X=Xba I, Xh=XhoI, S=Sst I. Not all sites for each enzyme are shown. Genomic clones were obtained from DU.528 DNA partially digested with MboI and cloned into EMBL 3. Chromosome 1 DNA was initially identified using chromosome 14 probes to identify the 1;14 translocation in DU.528 as previously described.

B. Northern blot analysis of 10 μg of total mRNA from human tissues and cell-lines. Probes are shown in A. Probe a detects both the normal and aberrant messages, probe b only detects the normal message because it comes from 3' of the translocation breakpoint. Northern transfers were performed using standard techniques. Note transcript of greater than 4 kb (below 28 S rRNA) in DU.528, recovery bone marrow and K562. cDNA libraries from these three sources were screened to obtain the cDNA clones described below. Note also the absence of signal in NL (T-cell line) and intense 2 kb (near the level of the 18S rRNA) abnormal fusion transcript in DU.528 compared with the less intense greater than 4 kb band. In poly A selected RNA an additional band greater than 5 kb was also seen. Hybridization to an actin probe revealed a comparable signal in all lanes (data not shown).

FIGS. 2A-D:

A nucleotide sequence and predicted amino acid sequence for an SCL gene. One cDNA library was constructed from BM mRNA obtained during recovery from chemotherapy. Both random hexamer priming and oligo-dT priming was performed and the cDNA was cloned into lambda-ZAPII (Stratagene). $10^6$ recombinant clones were screened and 11 overlapping inserts obtained. All were subcloned into pBluescript and sequenced in both directions using oligonucleotide primers.

One K562 cDNA library was obtained from Clontech and screened. A single 2.7 kb insert was obtained and subcloned into pGEM7Zf and sequenced in both directions. The predicted amino acid sequence begins at an ATG at nucleotide 81 (an ATG upstream of this runs into a termination codon within 12 nucleotides) and continues until the first in-frame TGA at nucleotide 723. Beyond this stop codon was a 297 bp region (nucleotides 836 to 1133) that was deleted in approximately one-half of the clones. The polyadenylation signal (AATAAA) is underlined. We now have an additional cDNA clone (58.3) which extends the open reading frame an additional 90 amino acids 5'. This is described in the text.

Figure 4:

FIGS. 3A-D:

A nucleotide sequence and predicted amino acid sequence for an SCL gene with a different 5' end than that of FIG. 2. The predicted amino acid sequence begins at the first nucleotide of this cDNA and continues until the first inframe TGA (nucleotide 619). An alternate carboxy-terminus was predicted from analysis of DU.528 cDNA clones and was generated by a 100 bp deletion in the coding region (indicated by []). The alternate carboxy-terminus is shown in FIG. 4 and the "new" termination codon as a result of the frameshift is indicated (TER) (nucleotide 956).

FIG. 4:

Primer extension analysis maps the 5' extent of this SCL gene. A 21 bp anti-sense oligonucleotide primer (nucleotides 48 to 69 of FIG. 3) was labeled with $^{32}P$ ATP using polynucleotide kinase, purified on 8% polyacrylamide/7M urea gel, electroeluted and allowed to anneal to 5 μg of total RNA from DU.528 and the recovery BM RNA. This was performed in reverse transcriptase buffer (BRL) and as a negative control, the labeled oligonucleotide was reacted with 10 μg of yeast t-RNA (YtRNA). Following annealing, 20 units of Moloney murine leukemia virus reverse transcriptase (BRL) was added in the presence of 0.8 mM deoxynucleotides and 10μ of RNasin (Promega) and a 1 hr incubation at 37° C. was performed. The reaction was terminated by phenol extraction and ethanol precipitation, followed by electrophoresis on an 8% polyacrylamide/7M urea gel and autoradiography. Full length extension of approximately 160 bp suggests the 5' extent of the SCL gene. In longer exposures, several intermediate bands were also seen. Since this is a highly GC-rich region with potential for secondary structure formation, such bands may only represent strong stop sites for reverse transcriptase.

FIG. 5:

Amino acid sequence relationship between SCL and a variety of other proteins.

Comparison of amino acid residues of a predicted SCL gene product with regions of the achaete-scute, daughterless and twist genes of Drosophila and the immunoglobulin enhancer binding protein E12, MyoD, N-myc, L-myc, c-myc and Lyl-1. The conserved amino acid residues are boxed in. The hydrophilic domain and the two predicted amphipathic helices are indicted. Ψ indicates hydrophobic residues. After Murre et al. (8).

FIGS. 6A-C:

Nucleotide sequence and predicted amino acid sequences for an aberrant fusion SCL gene.

An oligo-dT primed cDNA library was constructed from DU.528 mRNA and cloned into lambda-gtl10. $10^6$ recombinant clones were examined and 14 clones identified using probe A (FIG. 1A). Six inserts were subcloned into pGEM7ZF and sequenced in both directions using oligonucleotide primers and dideoxy sequencing reactions.

Beyond the stop codon at 511 was a 297 bp region (nucleotides 728 to 1025) that was deleted in approximately one-half the clones. Further 3', the chromosome 1 sequences were replaced by the genomic D delta 3 sequences from chromosome 14 (boxed). The genomic chromosome 14 sequences (lower case) continued for 688 bp and terminated with a poly-A tail just beyond the genomic sequence AATACA (underlined). The cDNA sequence of the site of the translocation was identical to the genomic sequence and included four nucleotides of 'N-region' diversity (UPPER CASE, broken box) present in the genomic sequence (4).

Aside from two different amino termini, an additional protein with an altered carboxy-terminus was predicted by one DU.528 cDNA clone. A 100 bp deletion in the coding region (indicated []) resulted in a frameshift so that the stop codon at nucleotide 511 was out of frame and this new protein terminated at nucleotide 848. This predicts a larger protein in which the putative DNA-binding domain remains intact (see text).

DETAILED DESCRIPTION OF THE INVENTION

The gene of the present invention and the stem cell leukemia gene and differentiation affector which is coded by the gene of the present invention have various potential uses. It is probable that the stem cell leukemia gene and differentiation affector of the present invention is a DNA binding protein (polypeptide) which possesses hyperspecific cell type DNA binding properties. Thus, if the protein of the present invention is introduced into a cell, it will bind to portions of a gene or genes involved in the regulation of hematopoietic cell growth and differentiation. Judging from the role of related proteins in other systems, it is most likely that this gene and gene product function as a positive regulator of hematopoietic growth and development. However, it is also possible that this gene could have specific and related negative regulatory functions mediated via the same DNA binding capacity.

1. The gene of the present invention is a "marker" for early hematopoietic differentiation. As shown in Table 1, certain types of cells express the gene of the present invention. Thus, identification of the gene and/or cells which express the gene could be used to diagnose hematopoietic malignancy, to classify hematopoietic malignancies, to diagnose bone marrow failure disorders [either caused and characterized by lack or aberrant expression of the gene (category 1) or characterized by overexpression of the gene as a means of overcoming a different defect (category 2)] and to classify bone marrow failure disorders. Such disorders would include, for example, aplastic anemias and leukemias.

2. Knowledge of the structure and DNA-binding function of the encoded protein provides a plausible target for drug therapy for the above mentioned disorders. A drug might exist or might be developed which specifically enhances or inhibits the function of this protein. Knowledge of the precise sequence bound by the protein provides an obvious approach to targeted drug therapy.

3. A transgenic mammal, specifically at present, a transgenic mouse, is being made which contains the gene of the present invention.

4. The protein of the present invention has uses similar to uses of known growth factors such as GMCSF, CSF and IL-3. For example, the protein may be useful to help patients recover from insults to bone marrow. More specifically, if a person is exposed to radiation which damages the white blood cells or if the patient is treated by chemotherapy which also may damage white blood cells, the protein of the present invention could be administered to the patient to help the patient produce additional white blood cells mediated specifically via its action and influence within the bone marrow stem cell compartment. The dose and route of administration of the protein of the present invention would be approximately equal to doses and routes of administration used for the above-mentioned growth factors.

5. It may also be possible to incorporate the gene of the present invention into a vector which infects the patient's cells. The infection of the patient's cells may be carried out in vivo or in vitro. The vector would express the protein which would then bind to the appropriate DNA sequence in the cell to cause the desired therapeutic effect. If the vector infects the cells in vitro, the cells could be returned to the patient for the desired therapeutic effect.

6. It is also possible to package the protein in a form which can be taken up by a cell, e.g., by encapsulating the protein with liposomes.

7. If it is determined that the protein of the present invention is a positive regulator, the protein would be delivered to cells by either infecting the cells with a vector which expresses the protein or by packaging the polypeptide for delivery to the cells. The polypeptide would then bind to the appropriate DNA which would cause the cells to proliferate and proceed along a hematopoietic developmental pathway.

8. It is also possible that an anti-sense sequence which binds to single stranded RNA corresponding to the gene of the present invention could be made whereby the anti-sense sequence would bind to single stranded RNA to prevent expression of the protein.

Sequence of a Normal SCL Gene:

Initial experiments were performed to obtain clones of the normal SCL gene for nucleotide sequence determination. Thus, normal tissues were examined as potential sources of RNA for construction of a cDNA library. Using probes derived from the region on chromosome 1 involved in the 1;14 translocation in DU.528, a transcript of greater than 4 kb (just below the 28 S ribosomal RNA, rRNA) was observed in normal tissues (FIG. 1). In the stem-cell leukemia, DU.528, the predominant transcript was approximately 2 kb. In addition, however, there was an approximately 4 kb transcript that was slightly smaller than that observed in normal tissues.

Among the normal tissues examined, a particularly high level of SCL expression was noted in bone marrow (BM) during recovery from chemotherapy. A cDNA library was therefore constructed from BM mRNA obtained from a patient with Ewing's sarcoma with no BM involvement. The BM was harvested during recovery from chemotherapy prior to autologous BM transplantation. The BM sample was hypercellular and normal immature myeloid elements predominated. There was no evidence of malignant cells. An oligo-dT and random-hexamer-primed cDNA library was constructed in lambda-ZAPII (Stratagene, LaJolla, Ca.). In addition, an oligo-dT primed cDNA library in lambda-gt10 from the CML/erythroleukemic cell line K562 was examined.

Twelve overlapping normal SCL clones were identified using the three probes from chromosome 1 shown in FIG. 1. One clone was from the K562 cDNA library (insert size 2.7 kb) and 11 from the recovery BM cDNA library. The inserts were overlapping and between 600-3000 bp. Inserts were subcloned into plasmid and the complete nucleotide sequence determined in both directions using synthesized oligonucleotide primers and the dideoxy chain termination method (5). An IBM PS2 with the PC-Gene (IntelliGenetics) program was used for data analysis and sequence comparison. Genbank and EMBL data bases were accessed via the Bionet National Computer Resource (6). Composite cDNA sequence for two SCL genes with alternative 5' ends were derived from the BM clones. They are shown in FIGS. 2 and 3 along with predicted portions of their amino acid sequences.

We could overlap our independent cDNA clones from the 3' poly A tail up to nucleotide 176 of FIG. 2 or nucleotide 72 of the FIG. 3 sequence shown. Primer extension analysis using a probe from nucleotides 48-69 of FIG. 3 yielded a specific band of approximately 160 nucleotides (90-100 nucleotides 5' of nucleotide 1 in FIG. 3) using mRNA from bone marrow, K562, and DU.528 (FIG. 4). A primer from nucleotides 121-139 (within the region of overlapping cDNA clones) yielded an extended product of a confirming approximate 230 nucleotides (also 90-100 nucleotides 5' of nucleotide 1 in FIG. 3). RNAse A protection assays using nucleotides 1-249 on RNA from K562 and normal bone marrow shows two protected species, one protecting the full 5' sequence shown in FIG. 3 (nucleotides 1-249), and one protecting the common overlapped region (nucleotides 72-249) mentioned above (data not shown). These data suggest that at least two separate 5' ends of the SCL gene exist, both of which include the 3' 4091 nucleotides starting at nucleotide 176 of FIG. 2 or nucleotide 72 of FIG. 3. A part of one putative distinct 5' end includes nucleotides 1-71 of FIG. 3 and nucleotides 1-175 of FIG. 2.

The major points to be made regarding features of the protein predicted by the SCL sequence follow from analyses of the body of the gene for which we have multiple overlapping clones from three different mRNA sources. Of the predicted greater than 4000 nucleotides in the full length message of this gene we have sequenced 4100-4200 in both directions and this is what is presented in FIGS. 2 and 3. An additional clone, 58.3, extends the coding sequence shown in FIG. 2 an additional 90 amino acids. The genomic exons encoding the additional sequence of this cDNA clone have been cloned by us as well. Before discussing the predicted proteins, some additional information on the cDNA structure follows.

A long open reading frame can be identified corresponding to the predicted proteins seen in FIGS. 2 and 3. This entire region is predicted to be a potential coding region with over 95% certainty using the method of Fickett (7). Our confidence in the correct reading frame of this gene stems from the predicted protein described below. The predicted proteins would be in the range of 30 kd.

The normal SCL gene had a 3.4 kb 3'-untranslated region. There were numerous stop codons in this region in all reading frames. Within this untranslated region, there was evidence of alternative splicing as manifested by a 297 bp region (nucleotides 940 to 1237 of FIG. 2 or 836 to 1133 of FIG. 3) that was deleted in half the clones. Moreover, when the BM and K562 sequences were compared, there were several nucleotide differences in the 3'untranslated region attributable to point mutations. The cDNA clones had a typical terminal polyadenylation signal sequence (AATAAA) and poly-A tail, thus delineating the 3' extent of the gene.

The SCL Gene Encodes a Potential DNA-Binding and Dimerization Motif:

Part of the predicted SCL gene product showed striking homology to a recently described putative DNA binding domain of a number of interesting proteins (8). These include genes important in neurogenesis, germ-layer development and sex-determination in Drosophila; Lyl-1, a newly described gene active in T-cell ALL (see below); MyoD, a gene important in myogenesis; Ig enhancer binding proteins, and three myc family genes. The identity between this region of the SCL gene and the analogous domain of the T8 achaete-scute gene of Drosophila was 53% over 58 amino acids and the region of homology extended over 120 amino acids. There was 30% identity with MyoD over 120 amino acids and 49 conservative amino acid substitutions. Amazingly, the identity between this region of the SCL gene and the analogous region of Lyl-1 was 84% over 58 amino acids with the non-identical residues representing mostly conservative changes. (FIG. 5).

The likely structure of this group of proteins has recently been described in detail (8). As with the other members of this group, the SCL gene product fits the proposed amphipathic helix-loop-helix structure. Preservation of this helix-loop-helix is believed to be important for DNA binding and may also allow dimerization of these proteins through their hydrophobic surfaces (8). The first helix of 12 amino acids has 2 highly conserved hydrophobic residues (leucine, phenylalanine) that appear on one side of the helix and a third residue whose hydrophobic character is preserved (isoleucine, valine, leucine). In the second helix of 13 amino acids, there are 5 highly conserved residues (all present in SCL) as well as a number of positions where additional hydrophobic residues are present. The sequence between the two helices contains one or more putative beta turns or loops. At the 5' end of the homologous region are 5 virtually identical hydrophilic residues and these highly conserved residues, as well as the intervening beta turn, are all predicted for the SCL gene product.

SCL Gene Expression Occurs Predominantly in Hematopoietic Tissues:

A variety of normal and malignant human tissues and cell lines were examined to assess the spectrum of SCL gene expression. A summary of these results is shown in Table 1.

TABLE 1

Spectrum of Expression of SCL

| Normal Tissues | | | |
|---|---|---|---|
| Fetal Liver (10 and 12.75 weeks) | + | Fetal Extremity (10 weeks) | − |
| Recovery BM (poly A & total) | + | Thymus tissue (<1 y.o child) | − |
| Term Placenta (poly A) | −/− | Brain (hippocampus) (poly A) | − |
| Neutrophils | +/− | Adult Liver (poly A) | − |
| PHA Stimulated peripheral blood | − | CD3-, CD4-, CD8-Thymocytes | − |
| Malignant Tissues | | | |
| AML, M5, CD7+ | + | CML | − |
| AML, M2 | + | preB-ALL | − |
| T-ALL | + | AML, M5, CD7+ | − |
| Burkitts Lymphoma (poly A) | − | Mycosis Fungoides (poly A) | − |
| ATL | − | SCC (poly A) | − |
| Cell Lines | | | |
| DU.528 (poly A & total) | + | H929 (poly A) | − |
| HSB-2 | + | HL60 | − |
| K562 | + | NL (poly A & total) | − |
| TE671 | + | NALL-1 | − |
| 592 (poly A) | + | CEM | − |
| DAOY | + | SB | − |
| SUP-T1 (poly A) | − | Hut 234 | − |

Spectrum of expression of the SCL gene. Northern blots were prepared using 10-20 μg of total RNA or 2 μg of poly A RNA from normal and malignant tissues and cell lines. All tissues were obtained in accordance with the requirements of the Ethics Committee of the National Institutes of Health. Malignant tissues examined included acute myeloid leukemia (AML) FAB M2 and M5 (positive for CD7). Samples from patients with chronic myeloid leukemia (CML) (n=1), acute lymphoblastic leukemia (ALL) (n=4, 1T, 3 preB), adult HTLV-1 positive T-cell leukemia (ATL) (n=1) and squamous cell carcinoma of lung (SCC) (n=1) were examined. Cell lines included CD7 positive, CD3, CD4, CD8 negative cells (DU.528, HSB-2), K562 ("erythroleukemia" of CML origin), HL60 ("promyelocytic leukemia"), SUP-T 1, NL, CEM (T-cell lines), H929 (plasma cell), NALL-1, SB (Bcells), Hut 234 (melanoma), 592 (small cell lung cancer), TE671 and, DAOY ("medulloblastoma") (16). Blots were examined with probes shown in FIG. 1A and were interpreted as positive (+) or negative (−) relative to the examples shown in FIG. 1B. A negative (−) result is not intended to be a claim for zero relevant mRNA, but only for a level beneath the sensitivity of this assay. In two cases (normal placenta and neutrophils) the interpretation was equivocal (+/−). Integrity of RNA samples was assessed by ethidium bromide staining and by hybridization with an actin probe.

All samples were assessed by Northern blot analysis of total mRNA or poly-A selected RNA and examples of positive and negative results are shown in FIG. 1. Of those tissues analyzed, expression of the SCL gene occurred predominantly in hematopoietic cells. In normal tissues, the highest levels of expression on a message per μg RNA basis were observed in fetal liver; higher than those seen in BM during recovery from chemotherapy. Control tissues from fetal extremities were negative, as were adult liver, brain, thymus and activated T-cells. Of the malignant tissues examined, two of three myeloid leukemias were positive. One was classified as FAB M2, one as FAB M5 but was also positive for the T-cell marker CD7. A T-cell ALL sample was positive while other B and T-cell tumors and the epithelial tumors examined were negative. These results were also supported by examination of cell lines. "Mature" B and T-cell lines were negative, while K562 and two CD7 positive, CD3, CD4, CD8 negative cell lines (DU.528 and HSB.2) were positive. In addition, three neuroendocrine cell lines (2 medulloblastoma, 1 small cell lung carcinoma) were positive for SCL gene expression. The SCL gene was therefore expressed predominantly in early normal hematopoietic tissues and in malignant tissues and cell lines with "primitive" hematopoietic characteristics, and in occasional "primitive" cell lines with neuroendocrine properties.

Sequence of an Aberrant 2 kb SCL Gene:

Experiments were performed to characterize the aberrant 2 kb fusion transcript in the stem-cell leukemia DU.528. An oligo-dT primed cDNA library from DU.528 mRNA was prepared in lambda-gt10 and screened with a chromosome 1 probe (probe A, FIG. 1). Inserts were between 500-2200 bp and were subcloned into plasmid for determination of nucleic acid sequence. A total of 14 clones were obtained and 6 sequenced in both directions. The composite nucleotide sequence and predicted amino acid sequence is shown in FIG. 6. The 297 bp region (between nucleotides 728 and 1025) of putative alternative splicing as noted previously for the normal BM cDNAs was deleted as determined by restriction endonuclease map analysis in 6/14 clones and was present in 8/14 clones. 325 nucleotides beyond this region the nucleotide sequence was of chromosome 14 origin. This sequence included the "diversity" (D) delta 3 gene and its flanking 3' genomic signal sequences and was identical to the previously described genomic sequence at the site of the chromosomal translocation. The sequences from chromosome 14 extended for an additional 293 bp. All clones had a poly-A tail immediately beyond the genomic sequence AATACA which served as a polyadenylation signal. In one clone an alternative chromosome 14 sequence was observed.

A splicing event occurred from the 5' end of the 3'-untranslated region of the normal SCL sequence to the "joining" (J) delta 1 gene and its flanking genomic sequences on chromosome 14.

A second form of the SCL gene product was predicted based on analysis of DU.528 cDNA clones. A deletion of 100 nucleotides in the coding region of one DU.528 cDNA clone resulted in a frameshift so that the TGA at 511 ceased to be a termination codon and a larger protein with a different carboxy-terminus was generated. This larger form of the SCL protein nevertheless retained intact and unaltered the previously described DNA-binding and dimerization motif.

Several other sites of uncertain significance were highlighted in both proteins by computer analysis of the predicted SCL gene product. These included potential phosphorylation sites (for cAMP/cGMP dependent kinases; for protein kinase C; for case in kinase II) and a possible ATP/GTP binding site.

Thus the chromosomal translocation in the human stem-cell leukemia served to disrupt the SCL gene and, as a result, a fusion transcript between sequences on chromosome 1 and chromosome 14 was generated. However, the translocation event into the 3'untranslated region preserved intact the putative SCL coding sequence.

Conclusions and Implications:

We have cloned and sequenced both a normal SCL gene and an aberrant form of this gene. The SCL gene was identified because of its involvement in a 1;14 translocation in a human stem-cell leukemia that is capable of differentiation into both lymphoid and myeloid cells. This translocation event served to disrupt the 3'end of the gene, leaving the coding region and therefore the protein product intact. Expression of the SCL gene is seen predominantly in hematopoietic tissues with the greatest levels being observed in "less mature" tissues and cell-lines.

In DU.528 a transcript is generated from both the allele involved in the translocation into the D delta 3 gene segment and the other allele. The approximately 4 kb transcript (which by analysis using probes 5' and 3' of the translocation could only come from the SCL chromosome 1 allele not involved in the 1;14 translocation) is smaller than the transcript observed in other tissues. In this regard it is noteworthy that the second chromosome 1 in DU.528 is also karyotypically abnormal in the region 1p33. It is possible that both SCL alleles in the DU.528 cell line have been altered by gross chromosomal rearrangements. The level of expression of the abnormal 2 kb fusion transcript is, however, as much as 20 fold greater by densitometric analysis than the larger transcript. It is possible, therefore, that the translocation event served to elevate the level of this fusion transcript by removing an element(s) in the 3'-untranslated region thereby stabilizing the transcript. In this regard, the percentage of A and T nucleotides in the 3' untranslated region of the normal transcript was 52.9% (versus 36% over the coding sequence) compared with 47.1% for C and G (64% within the coding sequence). Thus, the 3' region of the transcript is AT/AU rich and also contains two AUUUA consensus sequences believed to mediate mRNA degradation (11). Alternatively, it is possible that the translocation introduced a transcription enhancing element into the region of the SCL gene.

The predicted SCL gene product shows an intriguing homology to other DNA-binding proteins with conservation of a likely amphipathic helix-loop-helix DNA-binding and dimerization motif (8). The other proteins included in this group appear to play a critical role in differentiation and/or commitment of specific tissues. Thus, for example, MyoD is a nuclear phosphoprotein whose expression is restricted to proliferating myoblasts and differentiated myotubes. Expression of the MyoD cDNA in fibroblast or adipoblast cell lines converts them to myogenic cells (12). Similarly, the achaete-scute gene complex of Drosophila is central to neurological development—loss of these genes produces lack of neural elements; expression of these genes is restricted and precedes and parallels segregation of neuroblasts; a deficiency of these genes prevents appearance of at least one class of neuroblast (13). Other members of this group include the twist and daughterless genes of Drosophila (14) the myc family of genes (15) and Ig enhancer binding genes. In the latter, two protein forms are observed, probably the result of alternate exon usage (8). We have early indications that there may be alternate exon utilization at the 5' end of the SCL gene (compare the 5' ends of FIGS. 2 and 3). There is also a possibility based on sequence of one distinctive cDNA that an internal deletion may allow the formation of a slightly larger protein. In all predicted SCL proteins the DNA-binding motif is maintained.

Recently a new gene, Lyl-1, was described (16). It was discovered because of its presence at the site of a translocation breakpoint in the malignant cells of a patient with T-cell acute lymphoblastic leukemia. It is located on a different chromosome (chromosome 19) than SCL and is transcribed into a different size messenger RNA expressed in T-cells. Yet within its predicted helix-hoop-helix DNA binding region it demonstrates remarkable similarity to SCL. Its discoverers speculate on the role of Lyl-1 in neoplastic transformation. Its analogous method of discovery, involvement with the T-cell receptor locus, expression in T-cells, and striking similarity to SCL over a limited expanse of relevant protein domain leads to the speculation that these two genes may relate to each other in some cell type specific fashion.

In addition to the DNA-binding motif mentioned above, the predominant expression of SCL parallels, for example, the restricted expression of MyoD to myoblasts and achaete-scute to developing neuroblasts. Taken together, this restricted pattern of expression and the involvement of SCL in the stem-cell leukemia suggests strongly that the DNA-binding protein encoded by this gene may be important in hematopoietic differentiation or oncogenesis.

An *E. coli K*-12 derivative containing the plasmid vector pBluescript with a 3kb cDNA insert of the SCL gene including the coding sequence shown in FIG. 2 was deposited at the American Type Culture Collection, 12301 Parklawn Drive, Rockville, Md. 20852, on Nov. 2, 1989. This deposit has been assigned ATCC No. 68164. The cDNA insert includes the nucleic acid sequence shown in FIG. 2 from position 1 to somewhere between positions 3003 and 3102. The clone contains the entire putative coding sequence of one SCL gene and over 2000 bases of 3' untranslated region. The insert is cloned into the EcoRI site of the vector.

References and Notes:
1. I. R. Kirsch, J. A. Brown, J. Lawrence, S. J. Korsmeyer, C. C. Morton, Cancer Genet Cytogenet 18, 159 (1985).

2. P. C. Nowell, C. M. Croce, FASEB J. 2, 3054 (1988).
3. M. S. Hershfield, et al., Proc Natl Acad Sci USA 81, 253 (1984). J. Kurtzberg, S. H. Bigner, M. S. Hershfield, J Exp Med 162, 1561 (1985). The cell line DU.528 was kindly provided by Dr. J. Kurtzberg. All requests for the cell line should be addressed to Dr. J. Kurtzberg, Department of Pediatrics, Duke University Medical Centre, Durham N.C., 27710.
4. C. G. Begley et al., Proc Natl Acad Sci USA 86, 2031 (1989). C. G. Begley et al., J Exp Med 170, 339 (1989). C. G. Begley, P. D. Aplan, T. A. Waldmann, I. R. Kirsch, UCLA Symp Mol Cell Biol New Ser 120, (1989). (in press) During the preparation of this manuscript, a paper by Finger et al., Proc Natl Acad Sci USA 86, 5039 (1989) was published supporting the essential facts and features of our earlier reports.
5. F. Sanger, S. Nicklen, A. R. Coulson, Proc Natl Acad Sci USA 74, 5463 (1977).
6. W. R. Pearson, D. J. Lipman, Proc Natl Acad Sci USA 85, 2444 (1988).
7. J. W. Fickett, Nucleic Acids Res 10, 5303 (1982).
8. C. Murre, P. S. McCaw, D. Baltimore, Cell 56, 777 (1989).
9. R. Dalla-Favera, et al., Proc Natl Acad Sci USA 79, 7824 (1982). P. Leder et al., Science 222, 765 (1983). R. Taub et al., Proc Natl Acad Sci USA 79, 7837 (1982). J. M. Adams, S. Gerondakes, E. Webb, L. M. Corcoran, S. Cory, Proc Natl Acad Sci USA 80, 1982 (1983). Y. Tsujimoto, J. J. Yunis, L. Onorato-Showe, P. C. Nowell, C. M. Croce, Science 224, 1403 (1984). Y. Tsujimoto, L. R. Finger, J. J. Yunis, P. C. Nowell, C. M. Croce, Science 226, 1097 (1984).
10. N. Heisterkamp, K. Stam, J. Groffen, A. Deklein, G. Grosveld, Nature 315, 758 (1985). E. K Shtivelman, B. Lifshitz, R. Gale, E. Canaani, Nature 315, 550 (1985).
11. G. Shaw, R. Kamen, Cell 46, 659 (1986).
12. R. L. Davis, H. Weintraub, A. B. Lassar, Cell 51, 987 (1987). S. J. Tapscott, et al., Science 242, 405 (1988). S. F. Konieczny, A. S. Baldwin, C. P. Emerson Jr., UCLA Symp Mol Cell Biol New Ser 29, 21 (1985).
13. C. V. Cabrera, A. Martinez-Arias, M. Bate, Cell 50, 425 (1987). C. H. Dambly-Chaudiere, A. Ghysen, Genes Dev 1, 297 (1987). S. Romani, S. Campuzano, J. Modolell, EMBO J 6, 2085 (1989).
14. R. Villares, C. V. Cabrera, Cell 50, 415 (1987). M. Alonso, C. V. Cabrera, EMBO J 7, 2585 (1988). B. Thisse, C Stoetzel, C. Gorostiza-Thisse, F. Perrin-Schmitt, EMBO J 7, 2175 (1988). M. Candy, et al., Cell 55, 1061 (1988). C. Cronmiller, P. Schedl, T. Y. Cline, Genes Dev 2, 1666 (1988).
15. R. A. DePinho, K. S. Hatton, A. Tesfaye, G. D. Yancopoulos, F. W. Alt, Genes Dev 1, 1311 (1987). F. W. Alt et al., Cold Spring Harbor Symp Quant Biol 51, 931 (1986). K. Kelly, U. Siebenlist, Ann Rev Immunol 4, 327 (1986). J. Battey et al., Cell 34, 779 (1983). H. Persson, P. Leder, Science 225, 718 (1984). G. Ramsay, G. I. Evan, J. M. Bishop, Proc Natl Acad Sci USA 81, 7742 (1984).
16. J. D. Mellentin, S. D. Smith, M. L. Cleary, Cell 58, 77 (1989)
17. C. B. Lozzio, B. B. Lozzio, Blood 45, 321 (1975). P. F. Jacobsen, D. J. Jenkyn, J. M. Papadimitriou, J Neuropath Exp Neur, 44, 472 (1985). D. N. Carney, et al., Cancer Res, 45, 2913 (1985). F. Hecht, R. Morgan, B. K. M. Hecht, S.D. Smith, Science 226, 1445 (1984). S. D. Smith, et al., Blood 73, 2182 (1989). A. F. Gazdar, H. K. Oie, I. R. Kirsch, G. F. Hollis, Blood 67, 1542 (1986). R. A. Adams, A. Flowers, B. J. Davis, Cancer Res 28, 11221 (1968). G. E. Foley et al., Cancer 18, 522 (1965). R. A. Adams, Cancer Res 27, 2479 (1967). S. J. Collins, R. C. Gallo, R. E. Gallagher, Nature 270, 347 (1977). R. M. McAllister, et al., Int J Cancer 20, 206 (1977). We wish to thank Dr. M. Israel for providing samples of TE671 and DAOY mRNA for this analysis.

What is claimed is:

1. An isolated or purified SCL gene encoding a hematopoietic growth and differentiation affector which comprises the sequence

CGG CGT ATC TTC ACC AAC AGC CGG

GAG CGA TGG CGG CAG CAG AAT GTG

AAC GGG GCC TTT GCC GAG CTC CGC

AAG CTG ATC CCC ACA CAT CCC CCG

GAC AAG AAG CTC AGC AAG AAT GAG

ATC CTC CGC CTG GCC ATG AAG TAT

ATC AAC TTC TTG or a variant which codes for a homologous variant of said affector having less than eight amino acid changes, said amino acid changes being conservative amino acid changes, said gene being derived from human chromosome 1 abutting the translocation 1;14 breakpoint.

2. The SCL of claim 1, which comprises the sequence

| ATG | GCC | CCC | CCG | CAC | CTG | GTC | CTG | CTG | AAC | GCG | TCG | CCA | AGG | AGA | CGA |
|---|---|---|---|---|---|---|---|---|---|---|---|---|---|---|---|
| GCC | GCG | CGG | CCG | CAG | CGG | AGC | CCC | CAG | TCA | TCG | AAC | TGG | GCG | CGC | GCG |
| GAG | CCC | GGG | GGG | CGG | CCT | GCC | GGT | GGG | GGC | GGC | GCC | GCG | AGA | GAC | TTA |
| AAG | GCG | GCG | ACG | CGG | CGA | CGG | CCA | AGC | GCG | CCA | TCG | GGT | GCC | CAC | CAC |
| CGA | GCT | GTG | CAG | ACC | TCC | CGG | CCC | GCC | CCG | GCC | CCC | GCG | CCC | GCC | TCG |
| GTT | ACA | GCG | GAG | CTG | CCC | GGC | GAC | GGC | CGC | ATG | GTG | CAG | CTG | AGT | CCT |
| CCC | GCG | CTG | GCT | GCC | CCC | GCC | GCC | CCC | GGC | CGC | GCG | CTG | CTC | TAC | AGC |
| CTC | AGC | CAG | CCG | CTG | GCC | TCT | CTC | GGC | AGC | GGG | TTC | TTT | GGG | GAG | CCG |
| GAT | GCC | TTC | CCT | ATG | TTC | ACC | ACC | AAC | AAT | CGA | GTG | AAG | AGG | AGA | CCT |
| TCC | CCC | TAT | GAG | ATG | GAG | ATT | ACT | GAT | GGT | CCC | CAC | ACC | AAA | GTT | GTG |
| CGG | CGT | ATC | TTC | ACC | AAC | AGC | CGG | GAG | CGA | TGG | CGG | CAG | CAG | AAT | GTG |
| AAC | GGG | GCC | TTT | GCC | GAG | CTC | CGC | AAG | CTG | ATC | CCC | ACA | CAT | CCC | CCG |
| GAC | AAG | AAG | CTC | AGC | AAG | AAT | GAG | ATC | CTC | CGC | CTG | GCC | ATG | AAG | TAT |
| ATC | AAC | TTC | TTG | GCC | AAG | CTG | CTC | AAT | GAC | CAG | GAG | GAG | AGG | GGC | ACC |
| CAG | CGG | GCC | AAG | ACT | GGC | AAG | GAC | CCT | GTG | GTG | GGG | GCT | GGT | GGG | GGT |
| GGA | GGT | GGG | GGA | GGG | GGC | GGC | GCG | CCC | CCA | GAT | GAC | CTC | CTG | CAA | GAC |
| GTG | CTT | TCC | CCC | AAC | TCC | AGC | TGC | GGC | AGC | TCC | CTG | GAT | GGG | GCA | GCC |
| AGC | CCG | GAC | AGC | TAC | ACG | GAG | GAG | CCC | GCG | CCC | AAG | CAC | ACG | GCC | CGC |
| AGC | CTC | CAT | CCT | GCC | ATG | CTG | CCT | GCC | GCC | GAT | GGA | GCC | GGC | CCT | CGG |

TGA.

3. The SCL gene of claim 1, which comprises the sequence

```
AGG GGC CGG GCC GCC GCC GCT CAG GAC CGG GCC TCA AAA TGG CCA CAC
GCG TAC CCC CGT AGC GGA AAA ACC GGG TTC TTT GGG GAG CCG GAT GCC
TTC CCT ATG TTC ACC ACC AAC AAT CGA GTG AAG AGG AGA CCT TCC CCC
TAT GAG ATG GAG ATT ACT GAT GGT CCC CAC ACC AAA GTT GTG CGG CGT
ATC TTC ACC AAC AGC CGG GAG CGA TGG CGG CAG CAG AAT GTG AAC GGG
GCC TTT GCC GAG CTC CGC AAG CTG ATC CCC ACA CAT CCC CCG GAC AAG
AAG CTC AGC AAG AAT GAG ATC CTC CGC CTG GCC ATG AAG TAT ATC AAC
TTC TTG GCC AAG CTG CTC AAT GAC CAG GAG GAG GAG GGC ACC CAG CGG
GCC AAG ACT GGC AAG GAC CCT GTG GTG GGG GCT GGT GGG GGT GGA GGT
GGG GGA GGG GGC GCG CCC CCA GAT GAC CTC CTG CAA GAC GTG CTT
TCC CCC AAC TCC AGC TGC GGC AGC TCC CTG GAT GGG GCA GCC AGC CCG
GAC AGC TAC ACG GAG GAG CCC GCG CCC AAG CAC ACG GCC CGC AGC CTC
CAT CCT GCC ATG CTG CCT GCC GCC GAT GGA GCC GGC CCT CGG TGA.
```

4. An isolated or purified SCL gene encoding a hematopoietic growth and differentiation affecter which comprises the sequence

```
ACC ACC AAC AAT CGA GTG AAG AGG AGA CCT TCC CCC TAT GAG ATG GAG ATT
ACT GAT GGT CCC CAC ACC AAA GTT GTG CGG CGT ATC TTC ACC AAC AGC CGG
GAG CGA TGG CGG CAG CAG AAT GTG AAC GGG GCC TTT GCC GAG CTC CGC AAG
CTG ATC CCC ACA CAT CCC CCG GAC AAG AAG CTC AGC AAG AAT GAG ATC CTC
CGC CTG GCC ATG AAG TAT ATC AAC TTC TTG GCC AAG CTG CTC AAT GAC CAG
GAG GAG GAG GGC ACC CAG CGG GCC AAG ACT GCT GCG GCA GCT CCC TGG ATG
GGG CAG CCA GCC CGG ACA GCT ACA CGG AGG AGC CCG CGC CCA AGC ACA CGG
CCC GCA GCC TCC ATC CTG CCA TGC TGC CTG CCG CCG ATG GAG CCG GCC CTC
GGT GAT GGG TCT GGG CAA CAA GGA TCA GCC AGG AGG GCG TCC TTA GGC TGC
TGG GAT GGT GGG CTT CAG GGC AGG TGG GGT GAG AAT TGG GCG GCT CTG AAG
CAA GGC GGT GGA CTT GAA CTT TCC TGG ATG TCT GAA CTT TGG GAA GCC TTT
ACT GAC CCT GGG GCT GGC TTT TCT GTT TCC TGT ACC AGT AGG AGA TCA GAA
AAA TGG AGC AAA GTG GTA GGT ACT TTT TGT GAA GAC GGC ACG GTC TTC CCT
CTT CCC TCA GTC CCA AAT CCT TCC CAA GTA AGA GGC TGG AGT TGT CAC TGC
TTT TGG CCT GGA GTT TGG GAT CCC TGT CTT TCC TAA.
```

5. A vector, comprising: a replicable vector; and a DNA sequence corresponding to the SCL gene of claim 1 inserted into said vector.

6. The vector of claim 5, which is an expression vector capable of expressing said hematopoietic growth and differentiation affector.

7. The vector of claim 5, which is a plasmid.

8. A microorganism containing the vector of claim 5.

9. The microorganism of claim 9, which is identified as ATCC No. 68164.

10. The SCL gene of claim 1, which comprises the sequence

```
CGG CGT ATC TTC ACC AAC AGC CGG GAG CGA TGG CGG CAG CAG AAT GTG
AAC GGG GCC TTT GCC GAG CTC CGC AAG CTG ATC CCC ACA CAT CCC CCG
GAC AAG AAG CTC AGC AAG AAT GAG ATC CTC CGC CTG GCC ATG AAG TAT
ATC AAC TTC TTG.
```

11. An isolated or purified human SCL gene encoding a hematopoietic growth and differentiation affecter which comprises the sequence

```
                                                                    GCC TCG
GTT ACA GCG GAG CTG CCC GGC GAC GGC CGC ATG GTG CAG CTG AGT CCT CCC
GCG CTG GCT GCC CCC GCC GCC CCC GGC CGC GCG CTG CTC TAC AGC CTC AGC
CAG CCG CTG GCC TCT CTC GGC AGC GGG TTC TTT GGG GAG CCG GAT GCC TTC
CCT ATG TTC ACC ACC AAC AAT CGA GTG AAG AGG AGA CCT TCC CCC TAT GAG
ATG GAG ATT ACT GAT GGT CCC CAC ACC AAA GTT GTG CGG CGT ATC TTC ACC
AAC AGC CGG GAG CGA TGG CGG CAG CAG AAT GTG AAC GGG GCC TTT GCC GAG
CTC CGC AAG CTG ATC CCC ACA CAT CCC CCG GAC AAG AAG CTC AGC AAG AAT
GAG ATC CTC CGC CTG GCC ATG AAG TAT ATC AAC TTC TTG GCC AAG CTG CTC
AAT GAC CAG GAG GAG GAG GGC ACC CAG CGG GCC AAG ACT GGC AAG GAC CCT
GTG GTG GGG GCT GGT GGG GGT GGA GGT GGG GGA GGG GGC GGC GCG CCC CCA
GAT GAC CTC CTG CAA GAC GTG CTT TCC CCC AAC TCC AGC TGC GGC AGC TCC
CTG GAT GGG GCA GCC AGC CCG GAC AGC TAC ACG GAG GAG CCC GCG CCC AAG
CAC ACG GCC CGC AGC CTC CAT CCT GCC ATG CTG CCT GCC GCC GAT GGA GCC
GGC CCT CGG TGA
``` or a variant which codes for a homologous variant of said affecter having less than eight amino acid changes, said amino acid changes being conservative amino acid changes, said gene being derived from human chromosome 1 abutting the translocation 1;14 breakpoint.

12. The gene of claim 11, which codes for a protein having less than five conservative amino acid changes.

13. The gene of claim 11, which comprises the sequence

```
                                                                    GCC TCG
```

-continued

```
GTT ACA GCG GAG CTG CCC GGC GAC GGC CGC ATG GTG CAG CTG AGT CCT CCC
GCG CTG GCT GCC CCC GCC GCC CCC GGC CGC GCG CTG CTC TAC AGC CTC AGC
CAG CCG CTG GCC TCT CTC GGC AGC GGG TTC TTT GGG GAG CCG GAT GCC TTC
CCT ATG TTC ACC ACC AAC AAT CGA GTG AAG AGG AGA CCT TCC CCC TAT GAG
ATG GAG ATT ACT GAT GGT CCC CAC ACC AAA GTT GTG CGG CGT ATC TTC ACC
AAC AGC CGG GAG CGA TGG CGG CAG CAG AAT GTG AAC GGG GCC TTT GCC GAG
CTC CGC AAG CTG ATC CCC ACA CAT CCC CCG GAC AAG AAG CTC AGC AAG AAT
GAG ATC CTC CGC CTG GCC ATG AAG TAT ATC AAC TTC TTG GCC AAG CTG CTC
AAT GAC CAG GAG GAG GAG GGC ACC CAG CGG GCC AAG ACT GGC AAG GAC CCT
GTG GTG GGG GCT GGT GGG GGT GGA GGT GGG GGA GGG GGC GGC GCG CCC CCA
GAT GAC CTC CTG CAA GAC GTG CTT TCC CCC AAC TCC AGC TGC GGC AGC TCC
CTG GAT GGG GCA GCC AGC CCG GAC AGC TAC ACG GAG GAG CCC GCG CCC AAG
CAC ACG GCC CGC AGC CTC CAT CCT GCC ATG CTG CCT GCC GCC GAT GGA GCC
GGC CCT CGG TGA.                                        * * * * *
```